(12) United States Patent
Galambos et al.

(10) Patent No.: US 7,858,791 B2
(45) Date of Patent: Dec. 28, 2010

(54) PROCESS FOR THE PREPARATION OF CABERGOLINE

(75) Inventors: Janos Galambos, Budapest (HU); Laszlo Czibula, Budapest (HU); Ferenc Sebök, Mezökovacshaza (HU); Sandorné Balint, Budapest (HU); Ferencné Kassai, Budapest (HU); Györgyi Ignaczné Szendrei, Budapest (HU); Adam Demeter, Budapest (HU)

(73) Assignee: Richter Gedeon Vegyeszeti Gyar RT, Budapest (HU)

( * ) Notice: Subject to any disclaimer, the term of this patent is extended or adjusted under 35 U.S.C. 154(b) by 796 days.

(21) Appl. No.: 10/591,202

(22) PCT Filed: Mar. 2, 2005

(86) PCT No.: PCT/HU2005/000022

§ 371 (c)(1),
(2), (4) Date: Jun. 13, 2007

(87) PCT Pub. No.: WO2005/085243

PCT Pub. Date: Sep. 15, 2005

(65) Prior Publication Data

US 2007/0293677 A1      Dec. 20, 2007

(30) Foreign Application Priority Data

Mar. 4, 2004   (HU) .................................... 0400517

(51) Int. Cl.
C07D 457/04   (2006.01)
C07D 457/02   (2006.01)
(52) U.S. Cl. .......................................... 546/69; 546/67
(58) Field of Classification Search .................. 546/69, 546/67
See application file for complete search history.

(56) References Cited

U.S. PATENT DOCUMENTS 5,382,669 A * 1/1995 Candiani et al. ............... 546/69

OTHER PUBLICATIONS

Disposition and Urinary Metabolic Pattern of Cabergoline . . . by R. Battaglia et al. (Xenobiotica, 1993).

* cited by examiner

*Primary Examiner*—Charanjit S Aulakh
(74) *Attorney, Agent, or Firm*—Jonathan Myers

(57) ABSTRACT

A process for preparing cabergoline (I) from ergoline-8β-carboxylic acid ester (XIII) comprising the following steps. (XIII), (XVI), (XVII), (XVIII), (XIX), (I). The present case also relates to the intermediates (XVI), (XVII), (XVIII) and (XIX) as well as the polymorphic amorphous form of Cabergoline (I) and the production thereof.

-continued
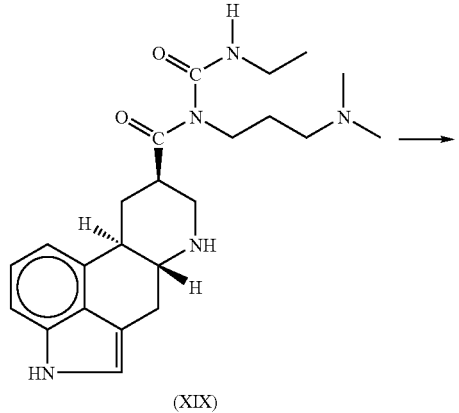
(XIX)
-continued
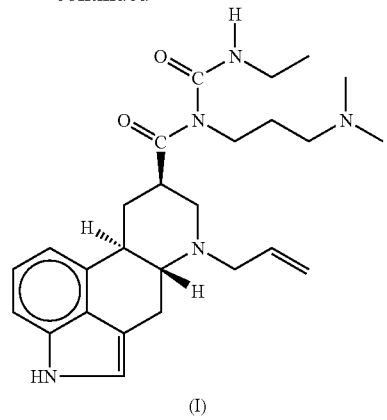
(I)
9 Claims, 3 Drawing Sheets

PROCESS FOR THE PREPARATION OF CABERGOLINE

CROSS REFERENCE TO RELATED APPLICATIONS

This application is the US national phase of PCT application PCT/HU2005/000022 filed 2 Mar. 2005 with a claim to the priority of Hungarian patent application P0400517 itself filed 4 Mar. 2004.

FIELD OF THE INVENTION

This invention relates to a new process for the preparation of cabergoline of formula (I), to novel intermediates used in this process, to the polymorphic amorphous form of cabergoline (I) and the preparation thereof.

BACKGROUND OF THE INVENTION

6-Allyl-N-[3-(dimethylamino)propyl]-N-[(ethylamino) carbonyl]-ergoline-8βcarboxamide—international non-proprietary name cabergoline—of formula (I)

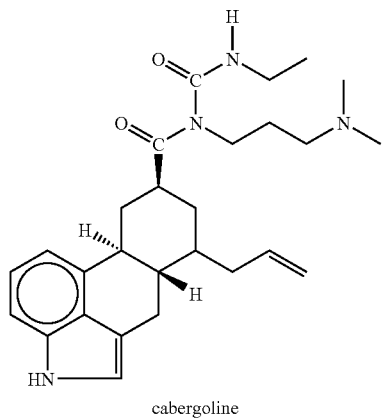

cabergoline is a potent dopamine agonist and is useful as anti-Parkinson drug and as prolactin inhibitor (*Eur. J. Med. Chem.* 1989, 24, 421-426 and U.S. Pat. No. 5,382,669).

Cabergoline (I) was firstly prepared according to U.S. Pat. No. 4,526,892 by reaction of 6-allyl-ergoline-8β-carboxylic acid (II) with 1-[3-(dimethylamino)propyl]-3-ethylcarbodiimide (EDC) (Scheme 1).

Scheme 1

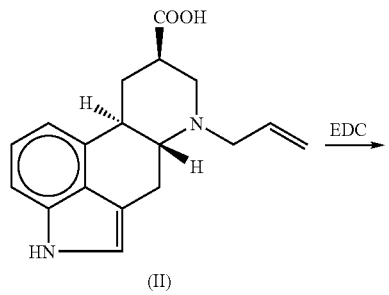

In this case both regioisomers (I) and (III) were obtained and the yield of the isolated cabergoline (I) is only approx. 21% as a consequence of isolation difficulties, considering that the yield of compound (II) prepared from (XIII) according to the state of the art is 70%.

*Eur. J. Med. Chem.* 1989, 24, 421-426 describes another method for the preparation of Cabergoline (I), which is based on the direct reaction of 6-allyl-N-[3-(dimethylamino)propyl]-ergoline-8β-carboxamide (IV) with ethyl isocyanate (EtNCO) (Scheme 2).

Scheme 2

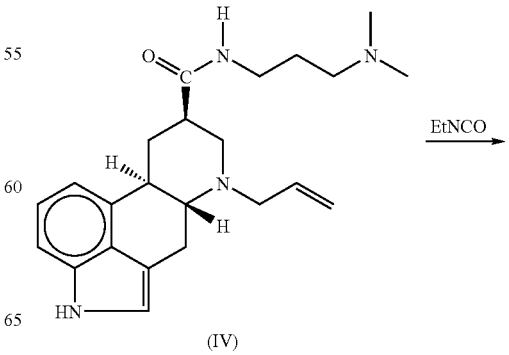

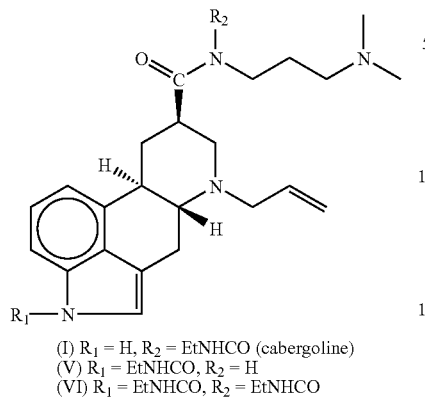

(I) R₁ = H, R₂ = EtNHCO (cabergoline)
(V) R₁ = EtNHCO, R₂ = H
(VI) R₁ = EtNHCO, R₂ = EtNHCO Since this reaction leads to equilibrium, it requires the use of a large excess of ethyl isocyanate (up to 40 equivalents) for reasonable conversion and must be conducted at above 100° C. in toluene for several hours. The use of large quantities of toxic ethyl isocyanate under drastic reaction conditions presents a serious hazard for the large-scale preparation of cabergoline (I). In addition, conversion to (I) is incomplete and competitive acylation of the indole nitrogen forming compounds (V) and (VI) occurs. This side reaction complicates the product purification and reduces the yield, which is only approx. 58%, considering that the yield of compound (IV) prepared from (XIII) according to the state of the art is 72%.

The method proposed in U.S. Pat. No. 5,382,669 and *Syn. Lett.* 1995, 605-606 showed that catalysis by copper salts in the presence of phosphine ligands permitted the ethyl isocyanate reaction to be run at room temperature with only 3 equivalents of ethyl isocyanate. However, despite of moderation in reaction conditions the conversion and the ratio of cabergoline (I) and the byproducts (V and VI) are not much different from the uncatalyzed thermal reaction. The yield is only approx. 48% and 57%, considering that the yield of compound (IV) prepared from (XIII) according to the state of the art is 72%.

*J. Org. Chem.* 2002, 67, 7147-7150 describes an ethyl isocyanate-free method for the production of cabergoline (I) that solves the problem of completing acylation of indole nitrogen, too.

The first step is the protection of indole nitrogen of amide (IV) preferably as tert-butyl carbamate (VII).

Extension of the amide side chain is done by deprotonation of compound (VII) with sodium hexamethyldisilazide (NaHMDS) followed by trapping the anion with phenyl chloroformate (PhOCOCl) to yield the phenyl carbamate (VIII).

Reaction of compound (VIII) with ethylamine hydrochloride (EtNH₂xHCl) gives BOC-cabergoline (IX) but also generates the ethylamide (X). The deprotection is done from the mixture of (IX) and (X) with 1N aqueous hydrochloric acid. The purified cabergoline (I) is then isolated by basification followed by chromatography on silica. (Scheme 3).

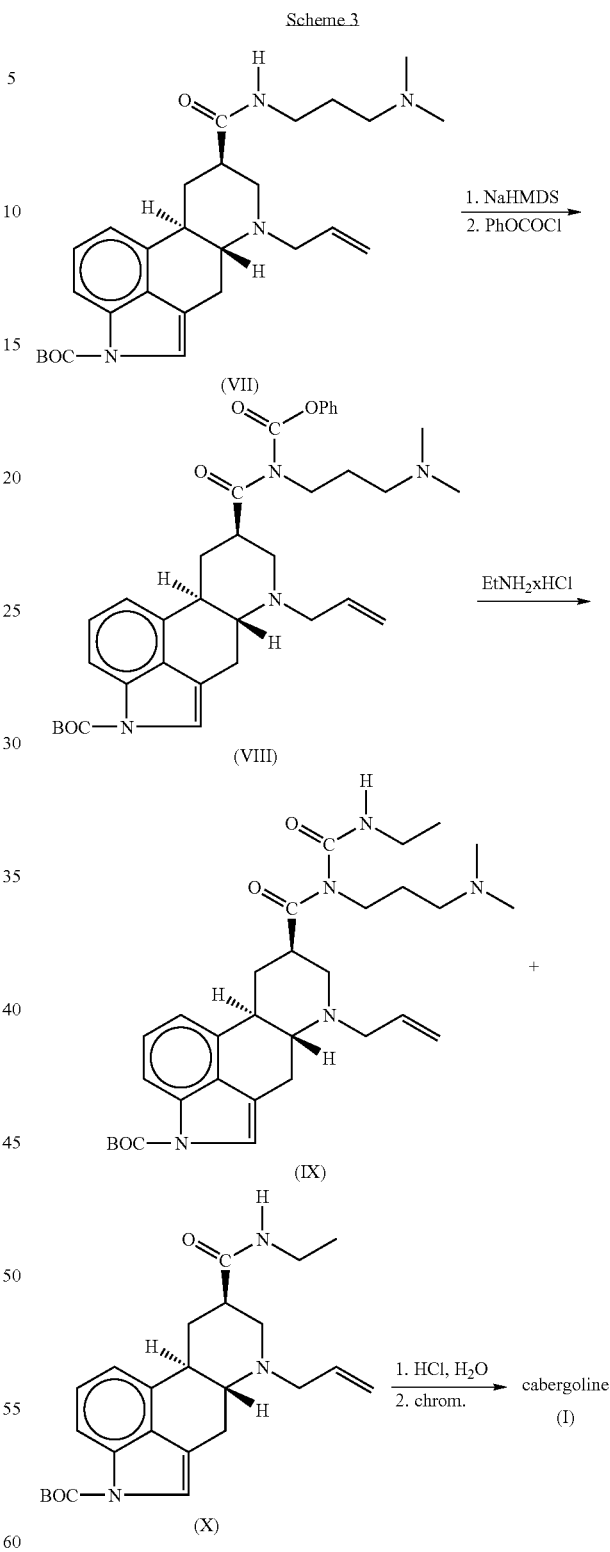

Scheme 3

In this approach the deprotonating step requires special cold reactor and strictly anhydrous circumstances. These requirements can hardly be satisfied in the course of large-scale preparation and the yield is only approx. 52%, considering that the yield of compound (VII) prepared from (XIII) according to the state of the art is 66%.

According to US 2002/0177709 A1 Patent Application cabergoline (I) may be prepared by silylating amide (IV) with a silylating agent (e.g. trimethylsilyl trifluoromethane sulfonate—TMSOTf), reacting the obtained product (XI) with ethyl isocyanate (EtNCO) followed by desilylation of intermediate (XII) (Scheme 4).

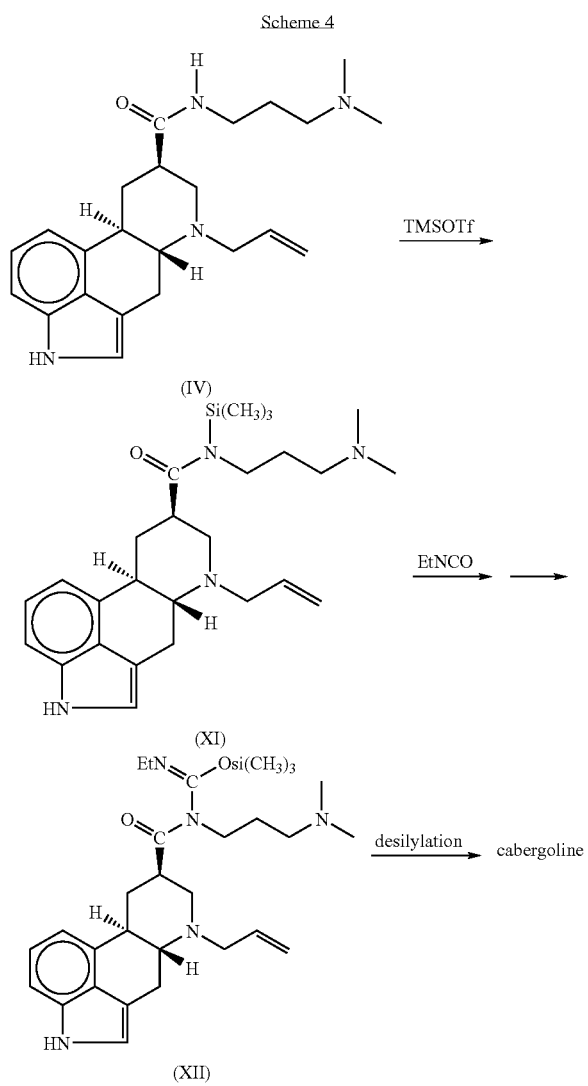

The disadvantage of this process is, that the silylating step requires strictly anhydrous circumstances. Otherwise, the reaction with ethyl isocyanate runs too long (24 hours) raising the safety hazard in the course of large-scale preparation and the yield is approx. 65%, considering that the yield of compound (IV) prepared from (XIII) according to the state of the art is 72%.

Several crystalline forms of Cabergoline (I) are known.

I L Farmaco 1995, 50 (3), 175-178 describes the preparation of crystalline form I. This solvated anhydrate product is crystallized from diethyl ether.

WO 01/70740 A1 Patent Application describes a new process for the preparation of crystalline form I from the new crystalline form V. The form V—which is toluene solvate—is prepared from the mixture of the purified cabergoline (I) with toluene and diethyl ether by a long-lasting complicated process, at low reaction temperature, and the yield is only 45%. The crystalline form I is prepared by drying the form V in vacuum.

WO 01/72746 A1 Patent Application describes the preparation of crystalline form VII from the crystalline form I. By this process the suspension of form I in n-heptane or 1,4-dioxane is stirred for 48 hours, and then the suspension was filtered to obtain the crystalline form VII. The yield is 45.2%.

WO 01/72747 A1 Patent Application describes the crystalline form II and a process for its preparation with approx. 70% yield by stirring the cabergoline (I) for several days in an organic solvent (eg. diethyl ether) at low temperature.

SUMMARY OF THE INVENTION

Surprisingly it was found that the preparation of cabergoline (I) with a method via new intermediates proposed by the present invention is commercially more advantageous than with the previously disclosed known methods due to the high yield (approx. 78%), the milder reaction conditions and the shorter reaction time. Another advantage of the use of these intermediates is that they have high hydrophobicity—in comparison to known intermediates bearing two basic function—so their purification by normal phase chromatography (if necessary) is highly effective due to the expanded difference in retention between them and the by-products.

The present invention relates to a process for preparing cabergoline (I) from ergoline-8β-carboxylic acid $C_{1-4}$ alkyl esters via new intermediates and the polymorphic amorphous form of cabergoline (I).

The process comprises protecting the secondary amine and the indole nitrogen functions of ergoline-8β-carboxylic acid $C_{1-4}$ alkyl esters as carbamate derivatives, amidating the obtained protected compound with 3-(dimethylamino)propylamine, reacting the amide with ethyl isocyanate, cleaving the protecting groups and reacting the obtained deprotected secondary amine with an electrophyl allyl alcohol derivative to obtain cabergoline (I).

The present invention also relates to the new intermediates used in this process.

The invention also relates to the new amorphous form of cabergoline (I) and the preparation thereof.

DETAILED DESCRIPTION OF THE INVENTION

The invention relates to a process for preparing cabergoline (I) comprising the following steps:
(a) Reacting a compound of formula (XIII)—wherein $R_1$ represents a $C_{1-4}$ alkyl group—in the presence of a catalyst
  (i) with a compound of formula (XIV),

X—COOR$_2$  (XIV)

wherein $R_2$ represents an optionally substituted straight or branched $C_{1-6}$ alkyl group, X represents a bromine or chlorine atom, or
  (ii) with a compound of formula (XV),

O(COOR$_2$)$_2$  (XV)

wherein $R_2$ is a group as defined above for formula (XIV);
(b) reacting the obtained carbamate derivative of formula (XVI)—wherein $R_1$ and $R_2$ is a group as defined above—with 3-(dimethylamino)propylamine (DMAPA) in the presence of a catalyst;
(c) reacting the obtained ergoline-8β-carboxamide derivative of formula (XVII)—wherein $R_2$ is a group as defined above—with ethyl isocyanate (EtNCO) in the presence of ligand(s) and Ib and IIb metal group salt as catalyst, (d) reacting the obtained protected N-acylurea derivative of formula (XVIII)—wherein $R_2$ is a group as defined above—with a strong aqueous inorganic acid (aq./acid);

(e) reacting the obtained secondary amine of formula (XIX) with an electrophyl allyl alcohol derivative in the presence of a palladium or nickel containing catalyst and optionally in the presence of ligand(s) to form cabergoline (I).

The reaction procedure is shown in Scheme 5.

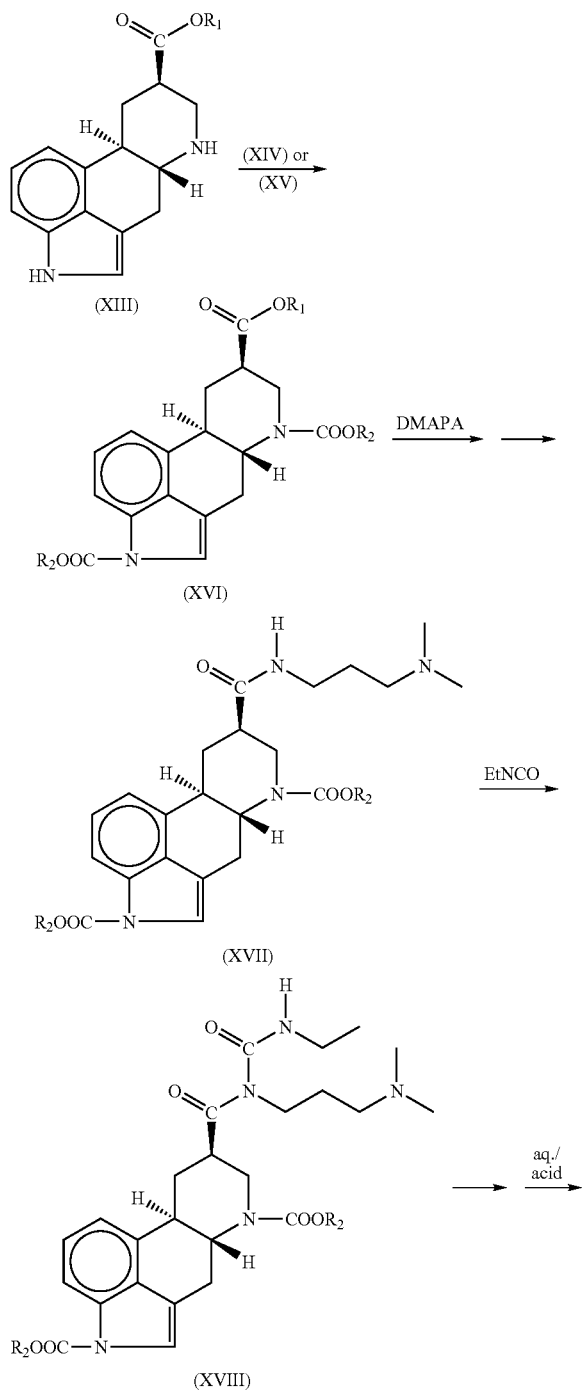

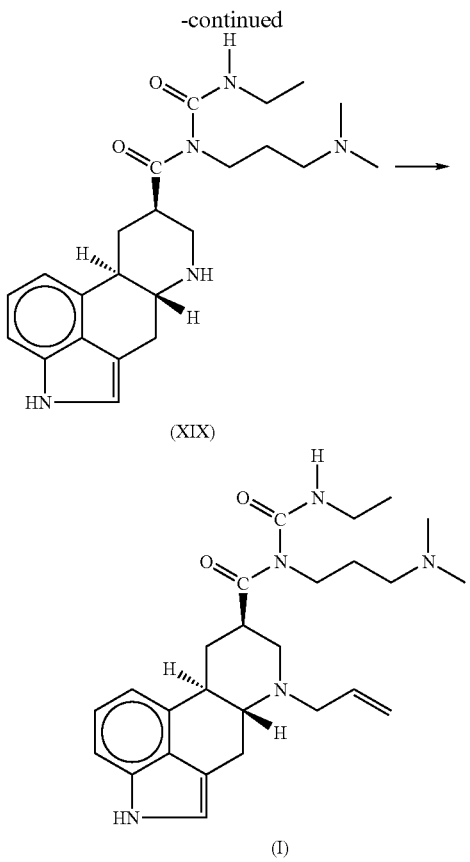

Step (a) of the process refers to reacting an ergoline-8β-carboxylic acid ester of formula (XIII) with a compound of formula (XIV) or (XV).

The starting materials, ergoline-8β-carboxylic acid esters of formula (XIII) can be prepared according to any method known in the state of the art: e.g. U.S. Pat. No. 4,166,182 or *Collect. Czech. Chem. Commun.* 1983, 48(5), 1483-1489.

Methods that serve for protection of both secondary amines and indole nitrogen are well known from the art. Thus, these functionalities can be protected e.g. as N-alkyl, N-aryl, N-silyl, N-sulfonyl derivatives or as carbamates. A number of protecting groups were examined, and it was found to be best to protect the starting material of formula (XIII) as the carbamate of formula (XVI).

Compounds of formula (XIV) and (XV) are commercially available or may be prepared by well known procedures or by procedures analogous to those described in the literature.

Compounds of formula (XIV) and (XV) may be used in a 2 to 10 fold molar amount, preferably from 2 to 5 fold molar amount, relative to the amount of ergoline-8β-carboxylic acid ester of formula (XIII).

The reaction may be carried out from −50° C. to the reflux temperature of the reaction mixture in a suitable aprotic solvent in the presence of an organic or inorganic base as catalyst.

Preferably the reaction step (a) is carried out at a temperature of from 0° C. to 50° C. in the presence of 4-dimethylaminopyridine catalyst in a hydrocarbon halide solvent.

Preferably $R_1$ is methyl and $R_2$ is tert-butyl.

Step (b) of the process refers to reacting the carbamate derivative of formula (XVI) obtained in the step (a) with 3-(dimethylamino)propylamine.

The amidation of ergoline-8β-carboxylic acid methyl ester derivatives containing a basic nitrogen in position 6 of the ergoline skeleton with 3-(dimethylamino)propylamine can be accomplished by know methods. The reactions can be carried out with a large excess of the amine (i) refluxing the reaction mixture for 10-12 hours without solvent (approx. at 135° C.) in the presence of acetic acid catalyst;

(ii) heating the reactants for 18 hours at 100° C. in ethylene glycol as a solvent with catalytic amount of 2-hydroxypyridine.

In both cases the yields are about 85% due to the decomposition reactions caused by the elevated temperature.

It has been found that the lack of the basic nitrogen in the D ring of the ergoline skeleton has a significant effect on the reaction time and temperature required in the amidation reaction.

So the reaction of carbamate derivatives of formula (XVI) with 3-(dimethylamino) propylamine carried out by known methods can be completed below 70° C. in a few hours. Due to the reduced temperature the obtained ergoline-8β-carboxamide derivative of formula (XVII) has high purity and the yield is over 95%.

The amidation may be accomplished at a temperature of from 40° C. to 70° C.

Catalysts accelerate the amidation reaction. All known catalysts can be used provided they do not hurt the tert-butoxycarbonyl protecting groups. Examples of catalysts are organic and inorganic bases such as alkali metal or earth metal hydroxides or carbonates, alkali metal or earth metal alcoholates, pyridine or its derivatives, tertiary amines, etc.; salts such as ammonium chloride, copper(II) acetate, magnesium chloride; and other catalysts such as boron tribromide, dimethylaluminium amides, mixed tin(II) amides or mixtures thereof.

The amidation can be carried out without solvent or in the presence of a suitable solvent.

Preferably the step (b) is carried out at a temperature of from 50° C. to 70° C. in an $C_{1-6}$ alkyl alcohol solvent in the presence of 2-hydroxypyridine catalyst.

The resultant amide of formula (XVII) may be used in the following step after isolation from the reaction mass following conventional procedures, or may be subjected to the subsequent step without isolation.

Step (c) of the process refers to reacting the ergoline-8β-carboxamide derivative of formula (XVII) obtained in the step (b) with ethyl isocyanate (EtNCO).

The ethyl isocyanate may be used in a 1 to 4 fold molar amount, preferably 2 to 3 molar amount relative to the amount of the amide (XVII).

Optionally, the reaction of amide (XVII) with ethyl isocyanate may be accelerated by metal catalysis in the presence of coordination compound(s). Suitable metal catalysts include Ib and IIb metal group salts, preferably copper(I) and copper (II) salts. Most preferred salts are copper(I) chloride, copper (II) chloride, copper(I) bromide and copper(I) iodide.

The ligands in the coordination compound(s) with Ib and IIb metals preferably contain phophorous, nitrogen and/or oxygen atoms. Examples of the ligands include triarylphophines, tertiary amines, nitrites, amides and ether-type compounds. Preferred ligands are triarylphophines, most preferred ligands are triphenylphosphine and tri-p-tolylphophine.

The reaction is carried out in the presence of a suitable aprotic organic solvent from 0° C. to the reflux temperature of the reaction mixture.

Preferably the step (c) is carried out in hydrocarbon halide solvent, in the presence of copper(I) chloride and/or copper (II) chloride and/or copper(I) bromide and/or copper(I) iodide catalysts and triphenylphosphine or tri-p-tolylphosphine ligand at a temperature of from 30° C. to 50° C.

The reaction product may be isolated and purified following conventional procedures. As the obtained protected N-acylurea derivatives of formula (XVIII) have high hydrophobicity (in comparison to known intermediates bearing two basic function), their purification by normal phase chromatography (if necessary) is highly effective due to the expanded difference in retention between it and the by-products.

Step (d) of the process refers to reacting the protected N-acylurea derivative of formula (XVIII) obtained in the step (c), with a strong aqueous inorganic acid to form N-[3-(dimethylamino)propyl]-N-[(ethylamino)carbonyl]-ergoline-8β-carboxamide (XIX).

Methods cleaving the carbamate-type protecting groups from basic nitrogen and indole nitrogen are well known from the art, but not each is suitable for both purposes. Otherwise, with some commonly used methods (e.g. with formic acid or trichloroacetic acid) no significant conversion was observed, while other methods (e.g. with trifluoroacetic acid or trifluoromethanesulfonic acid) were not tolerated by the substrate (XVIII) and/or by the product (XIX).

It has been found that carbamate-type protecting groups of compounds (XVIII), can be readily removed in a clean reaction with strong aqueous inorganic acids. In this term the strong acid means an acid which has a pK value less than 2 in water. Examples for strong inorganic acid are hydrochloric acid, hydrobromic acid, sulfuric acid, hydrochloric acid.

The deprotection may be carried out from 0° C. to the reflux temperature of the reaction mixture.

Because of the basic nitrogen functionality, both substrate (XVIII) and product (XIX) are fully soluble in aqueous acidic medium so no organic solvent is required to accomplish the deprotection reaction.

Preferably the step (d) is carried out at a temperature of from 40° C. to 80° C. in aqueous hydrochloric acid.

The resultant compound of formula (XIX) may be used in the following step after isolation from the reaction mass following conventional procedures, or may be subjected to the subsequent step without isolation.

Step (e) of the process refers to reacting the obtained 6-deallyl-cabergoline of formula (XIX) with an electrophyl allyl alcohol derivative to form Cabergoline (I).

Due to the formation of considerable amount of quaternary ammonium derivatives the allylation of the secondary amine functionality of (XIX) can not be accomplished by commonly used allylating agents (e.g. allyl halides, allyl arylsulfonates, allyl alkylsulfonates). However, no quaternary by-products may be observed when the product (I) is produced by nucleophilic allylic substitution reaction. So the reaction of 6-deallyl-cabergoline (XIX) with an electrophyl allyl alcohol derivative in an organic solvent in the presence of palladium or nickel catalyst and ligand(s) yields Cabergoline (I) in high purity. Examples of electrophyl allyl alcohol derivative are allylic carboxylates such as allyl acetate or allyl benzoate and allyl phenyl ether.

The catalytic system may be homogeneous or heterogeneous, preferably the catalytic system is homogeneous.

Examples of heterogeneous catalyst are palladium on activated carbon or polystyrene in the presence of phosphorous containing ligands, palladium ligated by phosphinated polystyrene or phosphinated silica.

Examples for homogeneous catalyst are tetrakis(triphenylphosphine)palladium(0), tetrakis(triphenylphosphine)n- ickel, bis(cycloocta-1,5-diene)nickel, [1,4-bis(diphenyl-phosphino)butane]nickel, allyl palladium chloride dimer and cis,cis,cis-1,2,3,4-tetrakis-(diphenylphosphinometyl)cyclopentane.

The reaction may be carried out in a suitable aprotic organic solvent from 0° C. to the reflux temperature of the reaction mixture.

Preferably at step (e) the electrophyl allyl alcohol derivative is allyl acetate, the catalyst is tetrakis(triphenylphosphine)palladium(0), and the reaction is carried out in an aromatic hydrocarbon solvents at a temperature of from 20° C. to 50° C.

The reaction product may be isolated and purified following conventional procedures. The cabergoline (I) can be converted into pharmaceutically acceptable salts. The cabergoline (I) or pharmaceutically acceptable salts thereof, can be subsequently formulated with a pharmaceutically acceptable carrier or diluent to provide a pharmaceutical composition.

The intermediate compounds of formula (XVI), (XVII), (XVIII) and (XIX) are new.

Surprisingly it was found that if the chromatographically purified oily Cabergoline (I) is dissolved in a suitable organic solvent and from the obtained solution the solvent is partially removed several times in vacuum at a temperature of from 0° C. to 30° C. until the residue is not oily but solid product, a new polymorphic amorphous form of Cabergoline (I) is obtained which is identified by XRD, DSC and IR analytical methods.

The chemical purity of the polymorphic amorphous form of Cabergoline (I) obtained by the above method is >99.5% (HPLC).

The advantage of the process for production of amorphous Cabergoline (I) is the short technological time and the high yield which is practically quantitative.

Preferably the used solvent is acetone, methyl acetate or dichloromethane.

According to our analytical and pharmacological studies the polymorphic amorphous form of Cabergoline (I) is very stable, the dissolution rate and absorption properties of the amorphous form of Cabergoline (I) are favourable. So the use of the amorphous form of Cabergoline (I) in pharmaceutical compositions is advantageous in comparison to known crystalline forms.

The invention is illustrated further by the following non-limiting examples:

Example 1

Synthesis of 1,6-di(tert-butoxycarbonyl)-ergoline-8β-carboxylic acid methyl ester (XVI, $R_1$=methyl, $R_2$=tert-butyl)

To a solution of 13.05 g (48.2 mmol) of ergoline-8β-carboxylic acid methyl ester (XIII, $R_1$=methyl) in 400 ml of dichloromethane 20 ml of triethylamine, 1.0 g of 4-dimethylaminopyridine, 42.1 g (193.1 mmol) of di-tert-butyl dicarbonate was sequentially added, and the reaction mixture was stirred at 40° C. for 5 hours. The mixture was cooled to ambient temperature and it was washed with 3×100 ml of sodium chloride solution. The organic layer was dried over anhydrous sodium sulphate, and concentrated in vacuum. Crystallization from hexane gave 21.6 g (95.2%) of the title compound.

$^1$H NMR (CDCl$_3$, TMS, 500 MHz) δ 1.46 (s, 9H, N(6)-COOC(CH$_3$)$_3$); 1.66 (s, 9H, N(1)-COOC(CH$_3$)$_3$); 1.88 (td, 1H, J=13.1 Hz, 9.5 Hz, H$_β$-9); 2.81 (ddd, 1H, J=13.1 Hz, 3.7 Hz, H$_α$-9); 2.86-2.94 (m, 1H, H-8); 3.06 (ddd, 1H, J=14.9 Hz, 11.6 Hz, 2.1 Hz, H$_α$-4); 3.14 (td, 1H, J=13.2 Hz, 3.6 Hz, H-10); 3.31 (dd, 1H, J=15.1 Hz, 4.0 Hz, H$_β$-4); 3.65 (td, 1H, J=11.4 Hz, 4.0 Hz, H-5); 3.70 (dd, 1H, J=14.2 Hz, 5.6 Hz, H$_α$-7); 3.73 (s, 3H, COOCH$_3$); 3.92 (dd, 1H, J=14.2 Hz, 4.5 Hz, H$_β$-7); 7.03 (d, 1H, J=7.2 Hz, H-12); 7.20-7.30 (m, 2H, H-2, H-13); 7.80 (br d, 1H, H-14).

Example 2

Synthesis of N-[3-(dimethylamino)propyl]-1,6-di(tert-butoxycarbonyl)-ergoline-8β-carboxamide XVII, $R_2$=tert-butyl)

A mixture of 14.7 g (31.24 mmol) 1.6-di(tert-butoxycarbonyl)-ergoline-8β-carboxylic acid methyl ester (XVI, $R_1$=methyl, $R_2$=tert-butyl), 58.8 ml of 3-(dimethylamino) propyl-amine, 29.4 ml of 2-propanol and 3.68 g of 2-hydroxypyridine was stirred at 70° C. for 8 hours. The reaction mixture was cooled to ambient temperature, and 230 ml of dichloromethane was added. The resulting mixture was washed with 3×120 ml of sodium chloride solution. The organic layer was dried over anhydrous sodium sulphate. The dried solution was either subjected to the subsequent step without isolation of the product or it was concentrated in vacuum to give 16.4 g (97.1%) of the title compound.

$^1$H NMR (CDCl$_3$, TMS, 500 MHz) δ 1.47 (s, 9H, N(6)-COOC(CH$_3$)$_3$); 1.62 (td, 1H, J=13.1 Hz, 10.4 Hz, H$_β$-9); 1.67 (s, 9H, N(1)-COOC(CH$_3$)$_3$); 1.66-1.76 (m, 2H, CONHCH$_2$CH$_2$CH$_2$N(CH$_3$)$_2$); 2.25 (s, 6H, CONHCH$_2$CH$_2$CH$_2$N(CH$_3$)$_2$); 2.36-2.45 (m, 2H, CONHCH$_2$CH$_2$CH$_2$N(CH$_3$)$_2$); 2.75-2.83 (m, 1H, H-8); 2.98 (ddd, 1H, J=13.4 Hz, 8.2 Hz, 3.1 Hz, H$_α$-9); 3.05 (ddd, 1H, J=14.2 Hz, 11.8 Hz, 2.1 Hz, H$_α$-4); 3.13 (td, 1H, J=13.3 Hz, 3.6 Hz, H-10); 3.28 (dd, 1H, J=14.8 Hz, 3.9 Hz, H$_β$-4); 3.28-3.42 (m, 2H, CONHCH$_2$CH$_2$CH$_2$N(CH$_3$)$_2$); 3.60 (dd, 1H, J=14.8 Hz, 6.0 Hz, H$_α$-7); 3.65 (td, 1H, J=11.4 Hz, 3.9 Hz, H-5); 3.92 (dd, 1H, J=14.8 Hz, 3.7 Hz, H$_β$-7); 7.04 (d, 1H, J=7.4 Hz, H-12); 7.22-7.32 (m, 2H, H-2, H-13); 7.62 (t, 1H, J=5.0 Hz, CONHCH$_2$CH$_2$CH$_2$N(CH$_3$)$_2$); 7.79 (br, d, 1H, H-14).

Example 3

Synthesis of N-[3-(dimethylamino)propyl]-N-[(ethylamino)carbonyl]-1,6-di(tert-butoxycarbonyl)-ergoline-8β-carboxamide (XVIII, $R_2$=tert-butyl)

To a solution of 15.5 g (28.67 mmol) of N-[3-(dimethylamino)propyl]-1,6-di(tert-butoxycarbonyl)-ergoline-8β-carboxamide (XVII, $R_2$=tert-butyl) in 350 ml of dichloromethane 0.8 g of triphenylphosphine, 0.3 g of copper(I) chloride and 6.8 ml (86 mmol) of ethyl isocyanate was sequentially added, and the reaction mixture was stirred at 35° C. for 4 hours. The reaction mixture was concentrated in vacuum and the product was purified on a silica plug to give 16.9 g (96.4%) of the title compound.

$^1$H NMR (CDCl$_3$, TMS, 500 MHz) δ 1.19 (t, 3H, J=7.5 Hz, CONHCH$_2$CH$_3$); 1.46 (s, 9H, N(6)-COOC(CH$_3$)$_3$); 1.66 (s, 9H, N(1)-COOC(CH$_3$)$_3$); 1.78-1.96 (m, 2H, CONCH$_2$CH$_2$CH$_2$N(CH$_3$)$_2$); 1.98 (td, 1H, J=13.0 Hz, 9.9 Hz, H$_β$-9); 2.29 (s, 6H, CONCH$_2$CH$_2$CH$_2$N(CH$_3$)$_2$); 2.32-2.52 (m, 2H, CONCH$_2$CH$_2$CH$_2$N(CH$_3$)$_2$); 2.77 (ddd, 1H, J=13.2 Hz, 7.1 Hz, 3.7 Hz, H$_α$-9); 3.12-3.24 (m, 2H, H$_α$-4, H-10); 3.26-3.34 (m, 3H, H$_β$-4, CONHCH$_2$CH$_3$); 3.65 (td, 1H, J=11.7 Hz, 4.2 Hz, H-5); 3.50-3.88 (br m, 5H, H-8, H-7, CONCH$_2$CH$_2$CH$_2$N(CH$_3$)$_2$); 7.03 (d, 1H, J=7.5 Hz, H-12); 7.20-7.32 (m, 2, H-13); 7.79 (br d, 1H, H-14); 9.40 (br t, 1H, CONHCH$_2$CH$_3$).

Example 4

Synthesis of N-[3-(dimethylamino)propyl]-N-[(ethylamino)carbonyl]-ergoline-8β-carboxamide (XIX)

To 12.7 g (20.76 mmol) of N-[3-(dimethylamino)propyl]-N-[(ethylamino)carbonyl]-1,6-di(tert-butoxycarbonyl)-ergoline-8β-carboxamide (XVIII, R$_2$=tert-butyl) 230 ml of 4M aqueous hydrochloric acid was added, and the reaction was stirred at 35° C. for 2 hours. The reaction mixture was cooled to ambient temperature, 200 ml of dichloromethane was added and the pH was adjusted to 11 with concentrated aqueous ammonia solution. The organic layer was separated and the aqueous layer was extracted with 2×60 ml of dichloromethane. The combined organic layer was dried over anhydrous sodium sulphate. The dried solution was either subjected to the subsequent step without isolation of the product or it was concentrated in vacuum to give 8.1 g (94.8%) of the title compound.

$^1$H NMR (CDCl$_3$, TMS, 500 MHz) δ 1.19 (t, 3H, J=7.3 Hz, CONHCH$_2$CH$_3$); 1.80-1.92 (m, 3H, H$_β$-9, CONCH$_2$CH$_2$CH$_2$N(CH$_3$)$_2$); 2.27 (s, 6H, CONCH$_2$CH$_2$CH$_2$N(CH$_3$)$_2$); (t, 2H, J=6.7 Hz, CONCH$_2$CH$_2$CH$_2$N(CH$_3$)$_2$); 2.60 (br s, 1H, N(6)H); 2.68-2.90 (m, 4H, H$_α$-4, H$_α$-9, H-5, H-10); 2.97 (t, 1H, J=12.3 Hz, H$_β$-7); 3.07 (dd, 1H, J=14.5 Hz, 4.0 Hz, H$_β$-4); 3.26-3.42 (m, 4H, H$_α$-7, H-8, CONHCH$_2$CH$_3$); 3.74-3.92 (m, 2H, CONCH$_2$CH$_2$CH$_2$N(CH$_3$)$_2$); 6.84-6.90 (m, 2H, H-2, H-12); 7.10-7.20 (m, 2H, H-13, H-14); 8.16 (s, 1H, N(1)H); 9.45 (br t, 1H, CONHCH$_2$CH$_3$).

Example 5

Synthesis of 6-allyl-N-[3-(dimethylamino)propyl]-N-[(ethylamino)carbonyl]-ergoline-8β-carboxamide (1) (Cabergoline)

To a suspension of 9.0 g (21.87 mmol) N-[3-(dimethylamino)propyl]-N-[(ethylamino)carbonyl)-ergoline-8β-carboxamide (XIX) in 250 ml of toluene 0.5 g of tetrakis(triphenylphosphine)palladium(0) and 5 ml of allyl acetate was added, and the reaction mixture was stirred at ambient temperature for 2 hours. The resulting mixture was washed with 100 ml of water. The organic layer was dried over anhydrous sodium sulphate. The dried solution was concentrated in vacuum and the product was purified on a silica plug to give 9.1 g (92.3%) of the title compound.

$^1$H NMR (DMSO-d$_6$, TMS, 500 MHz) δ 1.10 (t, 3H, J=7.2 Hz, CONHCH$_2$CH$_3$); 1.47 (q, 1H, J=12.4 Hz, H$_β$-9); 1.62-1.72 (m, 2H, CONCH$_2$CH$_2$CH$_2$N(CH$_3$)$_2$); 2.15 (s, 6H, CONCH$_2$CH$_2$CH$_2$N(CH$_3$)$_2$); 2.20-2.30 (m, 2H, CONHCH$_2$CH$_2$CH$_2$N(CH$_3$)$_2$); 2.32-2.40 (m, 2H, H-5, H$_β$-7); 2.54 (dd, 1H, J=14.3 Hz, 11.2 Hz, H$_α$-4); 2.68-2.84 (m, 2H, H$_α$-9, H-10); 3.08 (ddd, 1H, J=11.3 Hz, 3.1 Hz, 1.8 Hz, H$_α$-7); 3.14-3.22 (m, 2H, CONHCH$_2$CH$_3$); 3.26 (dd, 1H, J=14.7 Hz, 7.3 Hz, H$_x$—N(6)CH$_2$CH=CH$_2$); 3.28-3.38 (m, 2H, H$_β$-4, H-8); 3.48 (dd, 1H, J=14.7 Hz, 5.8 Hz, H$_y$—N(6)CH$_2$CH=CH$_2$); 3.58-3.68 (m, 2H, CONCH$_2$CH$_2$CH$_2$N(CH$_3$)$_2$); 5.15 (d, 1H, J=10.3 Hz, H$_x$—N(6)CH$_2$CH=CH$_2$); 5.24 (d, 1H, J=17.2 Hz, H$_y$—N(6)CH$_2$CH=CH$_2$); 5.88-5.98 (m, 1H, N(6)CH$_2$CH=CH$_2$); 6.75 (d, 1H, J=7.0 Hz, H-12); 6.97 (s, 1H, H-2); 7.01 (t, 1H, J=7.5 Hz, H-13); 7.13 (d, 1H, J=8.0 Hz, H-14); 9.04 (t, 1H, J=5.0 Hz, CONHCH$_2$CH$_3$); 10.60 (s, 1H, N(1)H).

Example 6

Production of polymorphic amorphous form of Cabergoline (I)

a) 10 g of chromatographically purified oily Cabergoline (I) was dissolved in 50 ml of acetone. The solution was concentrated in vacuum at 25-30° C. to approx. 15 g. The obtained oily residue was dissolved in 40 ml of acetone, and the solution was concentrated in vacuum at 25-30° C. to approx. 12 g. The obtained oily residue was dissolved in 30 ml of acetone again, and the solution was concentrated in vacuum at 25-30° C. to 10 g. The obtained solid Cabergoline (I) was dried in vacuum at 25-30° C. to solvent-free, to give 9.8 g (98%) of the title compound.

b) The same as in Example 6a, but employing methyl acetate as solvent, 9.85 g (98.5%) of the title compound was obtained.

c) The same as in Example 6a, but employing dichloromethane as solvent, 9.82 g (98.2%) of the title compound was obtained.

According to XRD, DSC, IR analytical studies the crystalline form of the product is amorphous.

X-Ray Powder Diffraction (XRD):

XRD was performed by using Philips PW 1840 Compact powder diffractometer.

Differential Scanning Calorimeter (DSC):

The DSC investigations were determined on Mettler Toledo DSC 821 Instrument.

Figure 1:
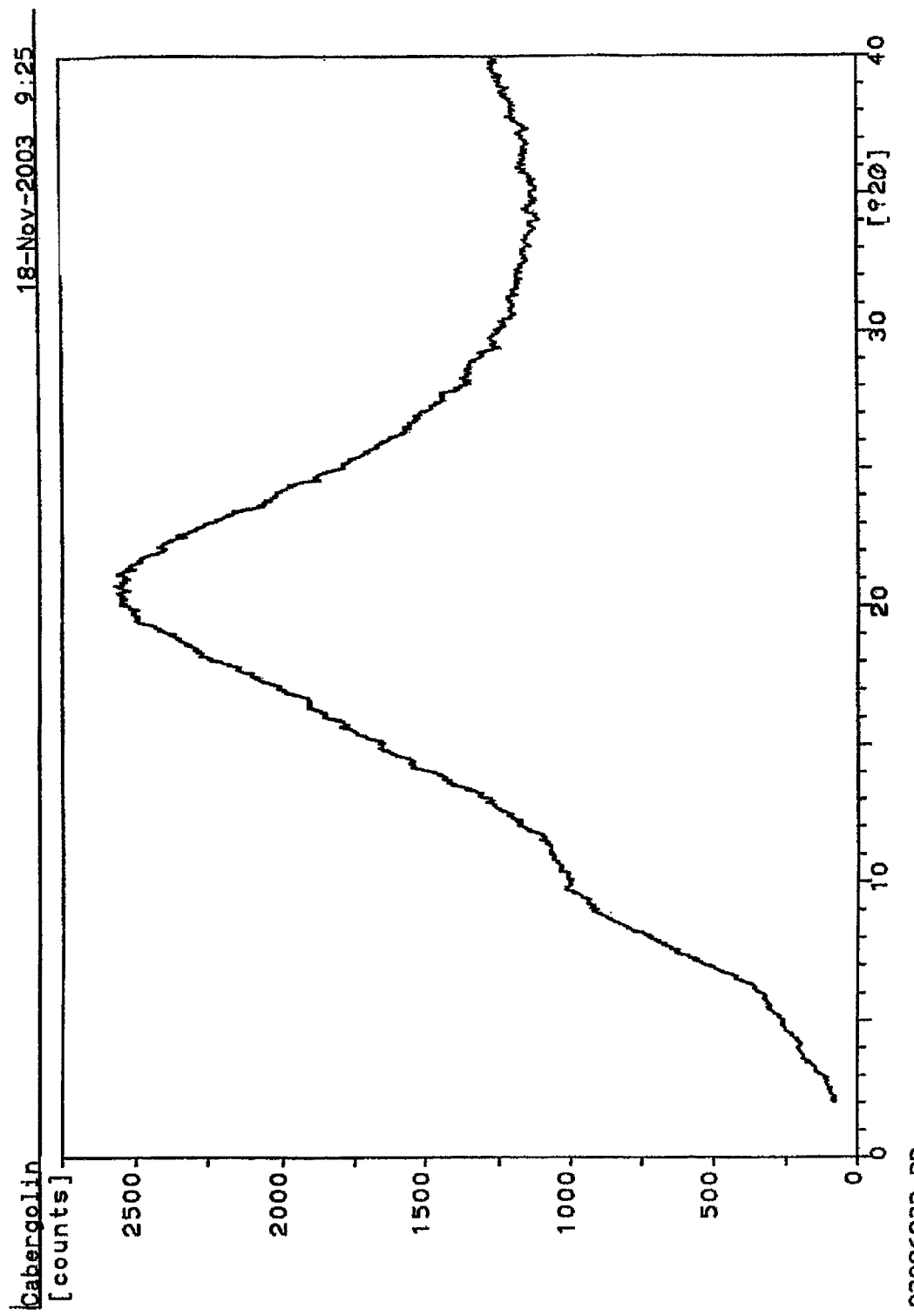
FIG. 1 shows the XRD Spectra of amorphous form of Cabergoline (I).
Figure 2:
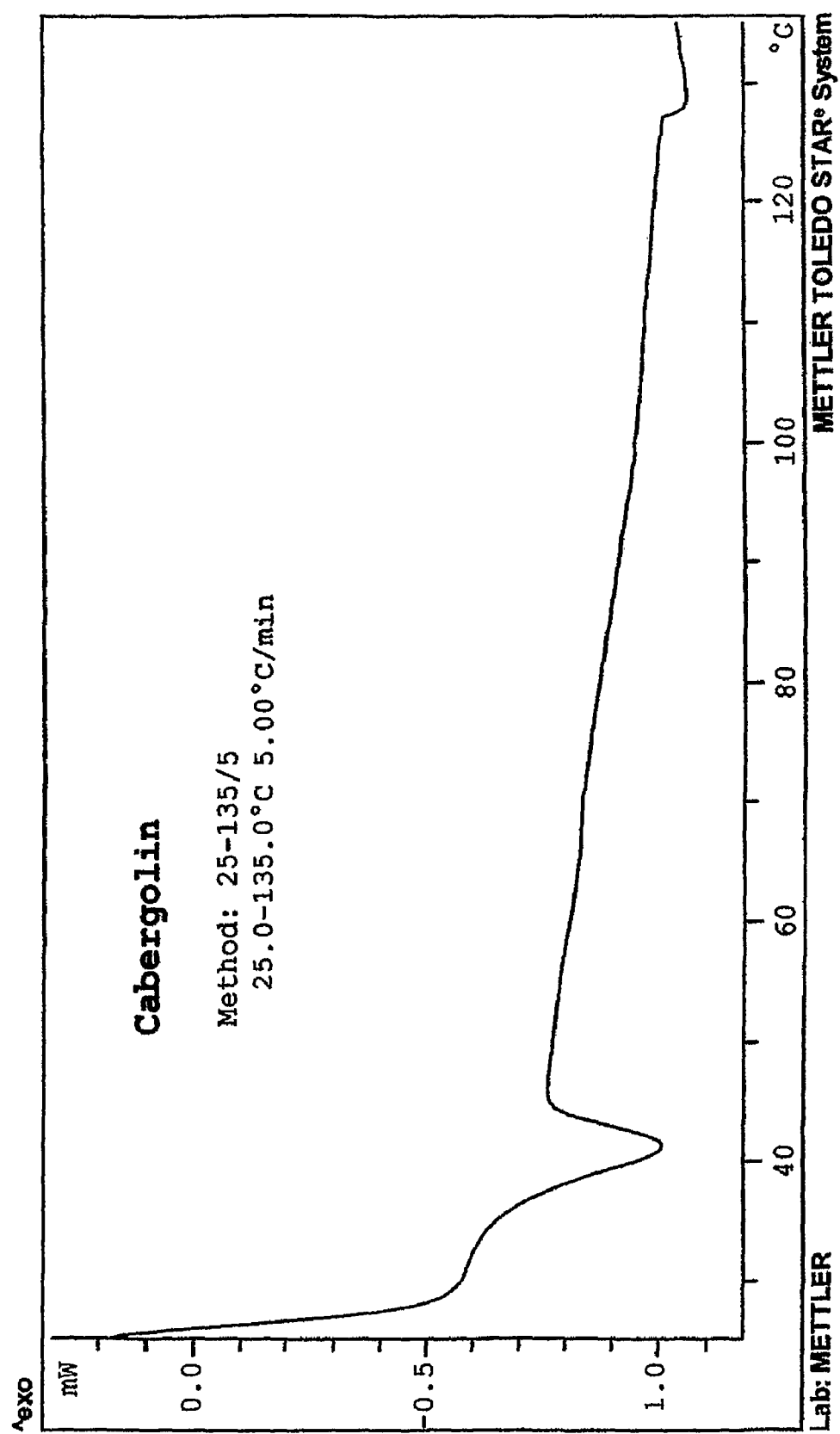
FIG. 2 shows the DSC Spectra of amorphous form of Cabergoline (I).
Figure 3:
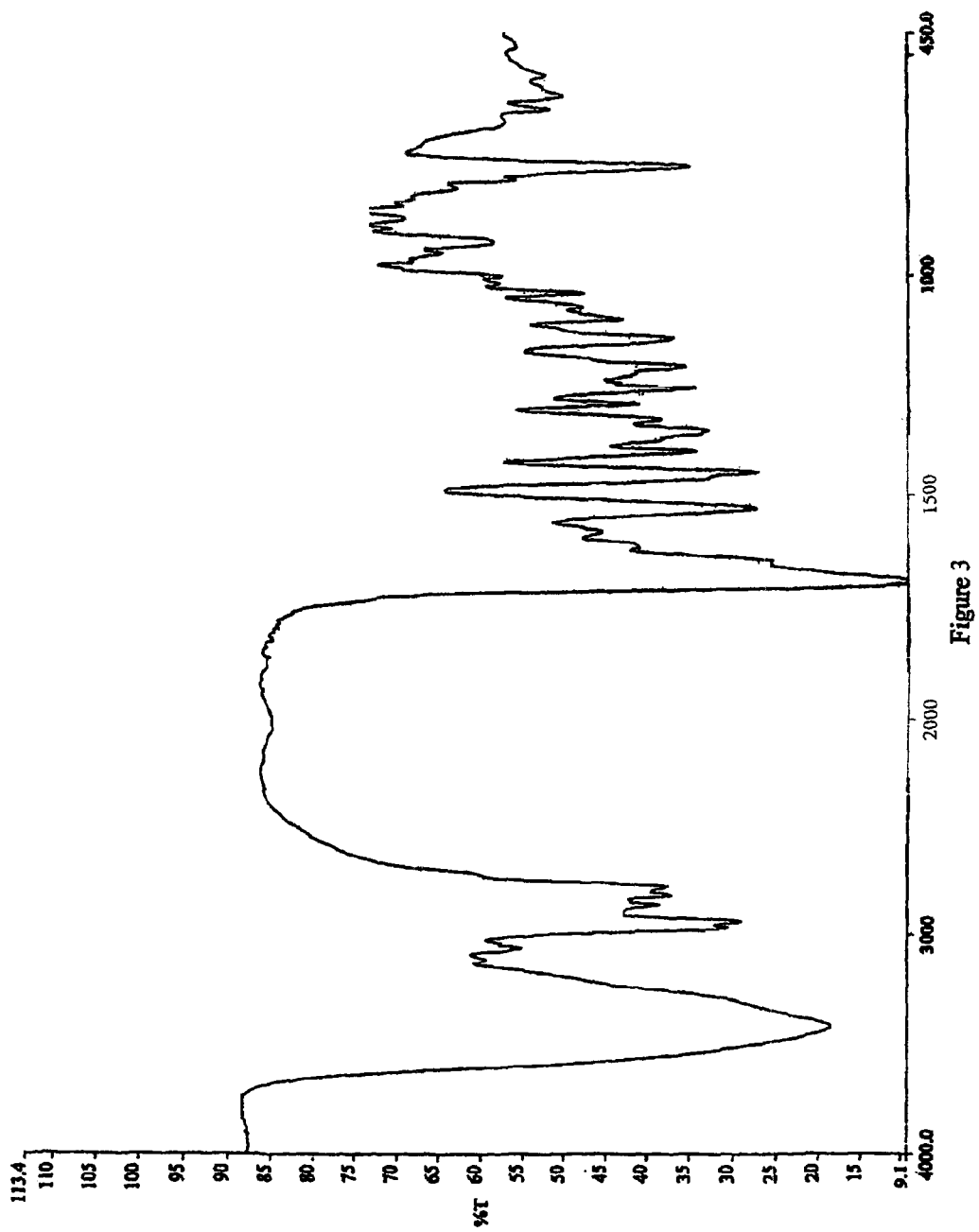
FIG. 3 shows the IR Spectra of amorphous form of Cabergoline (I).

The invention claimed is:

1. A process for preparing cabergoline (I)

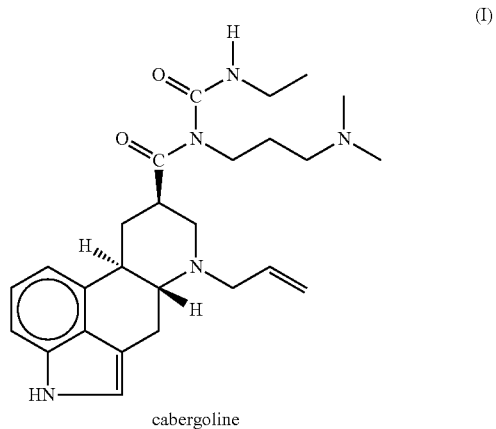

cabergoline comprising the following steps:

a) reacting the compound of formula (XIII)

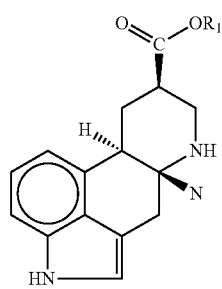

wherein $R_1$ is a $C_{1-4}$ alkyl group, in the presence of a catalyst i) with a compound of formula (XIV), X—COOR$_2$ (XIV)
wherein $R_2$ is an optionally substituted straight or branched $C_{1-6}$ alkyl group,
X represents a bromine or chlorine atom, or (ii) with a compound of formula (XV), O(COOR$_2$)$_2$ (XV) wherein $R_2$ is a group as defined above for formula (XIV);

b) reacting the obtained carbamate of formula (XVI)

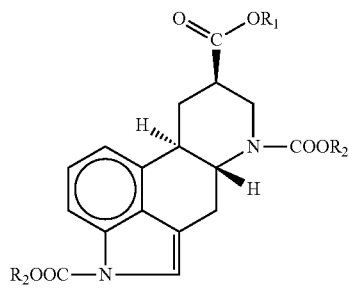

wherein $R_1$ and $R_2$ is a group as defined above, with 3-(dimethylamino)propylamine in the presence of a catalyst;

c) reacting the obtained ergoline-8β-carboxamide of formula (XVII)

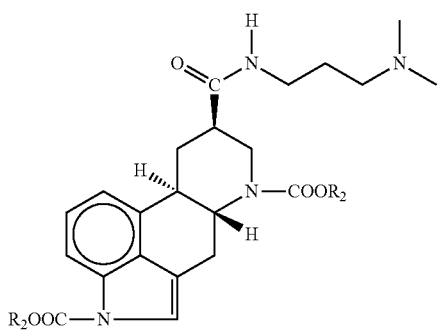

wherein $R_2$ is a group as defined above, with ethyl isocyanate in the presence of ligand(s) and Ib and IIb metal group salt catalyst;

d) reacting the obtained protected N-acylurea of formula (XVIII)

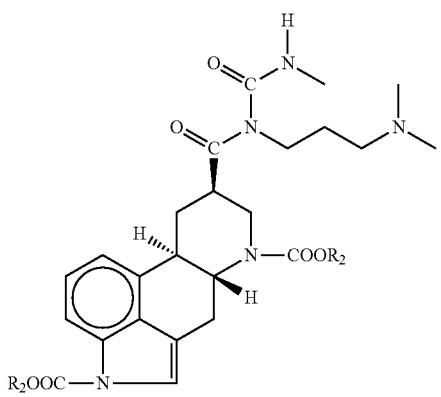

wherein $R_2$ is a group as defined above, with a strong aqueous inorganic acid; and e) reacting the obtained secondary amine of formula (XIX)

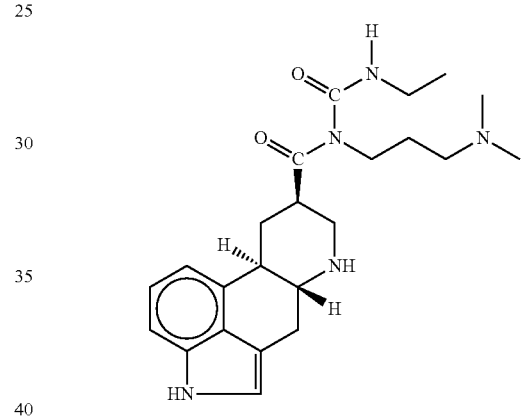

with an electrophilic allyl alcohol in the presence of a palladium or nickel containing catalyst and optionally in the presence of ligand(s) to form cabergoline (I).

2. A process according to claim 1 wherein $R_1$ is methyl and $R_2$ is tert-butyl.

3. A process according to claim 1 wherein step (a) is carried out at a temperature of from 0° C. to 50° C. in the presence of 4-dimethylaminopyridine catalyst in a hydrocarbon halide solvent.

4. A process according to claim 1 wherein step (b) is carried out at a temperature of from 50° C. to 70° C. in an $C_{1-6}$ alkyl alcohol solvent in the presence of 2-hydroxypyridine catalyst.

5. A process according to claim 1 wherein step c) is carried out in hydrocarbon halide solvent, in the presence of copper (I) chloride and/or copper(II) chloride and/or copper(I) bromide and/or copper(I) iodide catalysts and triphenylphosphine or tri-p-tolylphosphine ligand at a temperature of from 30° C. to 50° C.

6. A process according to claim 1 wherein step (d) is carried out at a temperature of from 40° C. to 80° C. in aqueous hydrochloric acid.

7. A process according to claim 1 wherein at step (e) the electrophilic allyl alcohol is allyl acetate, the catalyst is tetrakis(triphenyl-phosphine) palladium(0), and the reaction is carried out in an aromatic hydrocarbon solvent at a temperature of from 20° C. to 50° C.

8. A process according to claim 1 which further comprises the following steps:

(f) chromatographically purifying the Cabergoline of the Formula (I) to obtain Cabergoline as an oily solid product;

(g) dissolving the Cabergoline obtained as an oily solid product in an organic solvent; and (h) partially removing the organic solvent from the Cabergoline in several steps under vacuum at a temperature of from 0° C. to 30° C., to obtain a non-oily solid Cabergoline product.

9. A process according to claim 8 wherein the organic solvent employed during step (g) is acetone, methyl acetate or dichloromethane.

* * * * *